(12) United States Patent
Byrne

(10) Patent No.: US 11,808,710 B2
(45) Date of Patent: Nov. 7, 2023

(54) METHODS AND SYSTEMS FOR DETERMINING AN IONIC STRENGTH OF A DILUTE AQUEOUS SOLUTION

(71) Applicant: University of South Florida, Tampa, FL (US)

(72) Inventor: Robert H. Byrne, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 295 days.

(21) Appl. No.: 17/357,075

(22) Filed: Jun. 24, 2021

(65) Prior Publication Data

US 2021/0404972 A1    Dec. 30, 2021

Related U.S. Application Data

(60) Provisional application No. 63/043,885, filed on Jun. 25, 2020.

(51) Int. Cl.
*G01N 21/80* (2006.01)
*G01N 33/18* (2006.01)

(52) U.S. Cl.
CPC ............. *G01N 21/80* (2013.01); *G01N 33/18* (2013.01)

(58) Field of Classification Search
None
See application file for complete search history.

(56) References Cited

U.S. PATENT DOCUMENTS

| | | | |
|---|---|---|---|
| 5,925,572 A | 7/1999 | Byrne et al. | |
| 2006/0234388 A1* | 10/2006 | Bryne | G01N 21/0303 436/171 |

OTHER PUBLICATIONS

Manov, George G., et al. "Values of the constants in the Debye-Hückel equation for activity coefficients1." Journal of the American Chemical Society 65.9 (1943): 1765-1767.
Powell, Kipton J., et al. "Chemical speciation of environmentally significant heavy metals with inorganic ligands. Part 1: The Hg2+—Cl-, OH-, CO32-, SO42-, and PO43-aqueous systems (IUPAC Technical Report)." Pure and applied chemistry 77.4 (2005): 739-800.
Byrne, Robert H., and Jabe A. Breland. "High precision multiwavelength pH determinations in seawater using cresol red." Deep Sea Research Part A. Oceanographic Research Papers 36.5 (1989): 803-810.
Clayton, Tonya D., and Robert H. Byrne. "Spectrophotometric seawater pH measurements: total hydrogen ion concentration scale calibration of m-cresol purple and at-sea results." Deep Sea Research Part I: Oceanographic Research Papers 40.10 (1993): 2115-2129.
Zhang, H., & Byrne, R. H. (1996). Spectrophotometric pH measurements of surface seawater at in-situ conditions: absorbance and protonation behavior of thymol blue. Marine Chemistry, 52(1), 17-25. doi:10.1016/0304-4203(95)00076-3.
Hudson-Heck, Ellie, and Robert H. Byrne. "Purification and characterization of thymol blue for spectrophotometric pH measurements in rivers, estuaries, and oceans." Analytica chimica acta 1090 (2019): 91-99.
Byrne Jr, Robert H., and Dana R. Kester. "Inorganic Speciation of'Boron tn Seawater'." (1974) 119-127.
Mehrbach, Carl, et al. "Measurement of the apparent dissociation constants of carbonic acid in seawater at atmospheric pressure 1." Limnology and oceanography 18.6 (1973): 897-907.
Barbero L., Wanninkhof R., Dickson A. G., Carlson C. A., Key R. M., Becker S., Swift J. H., McNichol A., and Rodriguez C. (2018) Discrete profile measurements of dissolved inorganic carbon, total alkalinity, pH on total scale and other hydrographic and chemical data obtained during the R/V Roger Revelle Repeat Hydrography Cruise in the Indian Ocean: GO-SHIP Section 109N, (Expocode 33RR20160321) from Mar. 21, 2016 to Apr. 28, 2016 (NCEI Accession 0178637). NOAA National Centers for Environmental 620 Information. Dataset. https://doi.org/10.25921/f59c-dy18.
Bates N. R., Astor Y. M., Church M. J., Currie K., Dore J. E., Gonzalez-Davila M., Lorenzoni L., Muller-Karger F., Olafsson J. and Santana-Casiano J. M. (2014) A time-series view of changing surface ocean chemistry due to ocean uptake of anthropogenic CO2 and ocean acidification. Oceanography 27, 126-141. doi:10.5670/oceanog.2014.16.
Byrne R. H. (1987) Standardization of standard buffers by visible spectrometry. Anal. Chem. 59, 1479-1481. https://doi.org/10.1021/ac00137a025.
Byrne R. H. (2014) Measuring ocean acidification: new technology for a new era of ocean chemistry. Environ. Sci. Technol. 48, 5352-5360. doi:10.1021/es405819p.
Caldeira K. and Wickett M. E. (2003) Anthropogenic carbon and ocean pH. Nature 425, 365. doi: 10.1038/425365a.
Carter B. R., et al., (2017) Two decades of Pacific anthropogenic carbon storage and ocean acidification along Global Ocean Ship-based Hydrographic Investigations Program sections P16 and P02. Global Biogeochem. Cycles 31, 306-327. doi:10.1002/2016gb005485.
Dataset]Carter B. R., et al., (2018) Carbon dioxide, hydrographic and chemical data collected from profile discrete samples during the NOAA Ship Ronald H. 640 Brown cruise RB-16-06 along the GO-SHIP Repeat Hydrography Section P18 (Expocode 33RO20161119) in the Pacific Ocean from Nov. 19, 2016 to Feb. 3, 2017 (NCEI Accession 0171546). NOAA National Centers for Environmental Information. Dataset. https://doi.org/10.7289/v5cv4g1w.
Dataset]Cross J. N., et al., (2017) Dissolved inorganic carbon (DIC), total alkalinity, pH on total scale, dissolved organic carbon (DOC), chlorofluorocarbons (CFC-11, CFC-12), temperature, salinity and other hydrographic and chemical variables collected from discrete samples and profile observations during the R/V Ronald H. Brown cruise along the GO-SHIP Section P16N_2015, Legs 1 and 2 (EXPOCODEs 33RO20150410 and 33RO20150525) in the Pacific Ocean, from Apr. 10, 2015 to Jun. 27, 2015 (NCEI Accession 0163182). NOAA National Centers for Environmental Information. Dataset. https://doi.org/10.3334/cdiac/otg.go_ship_p16n_2015.

(Continued)

*Primary Examiner* — Lore R Jarrett
(74) *Attorney, Agent, or Firm* — Meunier Carlin & Curfman LLC

(57) ABSTRACT

Disclosed herein are methods for measuring the ionic strengths of the natural water sources. Also disclosed herein are systems used to measure an ionic strength of the natural water sources. More specifically disclosed herein are methods and systems utilizing spectroscopic pH measurements and calculations of the ionic strength as a function of the measured pH.

18 Claims, No Drawings

(56) References Cited

OTHER PUBLICATIONS

Dickson A. G. (1990) Standard potential of the reaction: AgCl(s)+1/2H2(g)=Ag(s)+HCl(aq), and and the standard acidity constant of the ion HSO4—in synthetic sea water from 273.15 to 318.15 K. J. Chem. Thermodyn. 22, 113-127. https://doi.org/10.1016/0021-9614(90)90074-Z.

Dickson A. G. (2010) The carbon dioxide system in seawater: Equilibrium chemistry and measurements. Guide to Best Practices for Ocean Acidification Research and Data Reporting, 17-40.

Dickson A. and Millero F. J. (1987) A comparison of the equilibrium constants for the dissociation of carbonic acid in seawater media. Deep Sea Res. Part A. Oceanogr. Res. Papers 34, 1733-1743. https://doi.org/10.1016/0198-0149(87)90021-5.

DOE (1994) Handbook of methods for the analysis of the various parameters of the carbon dioxide system in sea water; version 2, A. G. Dickson & C. Goyet, eds., ORNL/CDIAC-74.

Doney S. C., et al., (2012) Climate change impacts on marine ecosystems. Annu. Rev. Mar. Sci. 4, 11-37. doi:10.1146/annurev-marine-041911-111611.

Dataset]Feely R. A., Alin S. R., Hales B., Johnson G. C., Juranek L. W., Byrne R. H., Peterson W. T., Goni M., Liu X., and Greeley D. (2016) Dissolved inorganic carbon, pH, alkalinity, temperature, salinity and other variables collected from discrete sample and profile observations using Alkalinity titrator, CTD and other instruments from WECOMA in the Gulf of the Farallones National Marine Sanctuary, Monterey BayNational Marine Sanctuary and others from Aug. 12, 2011 to Aug. 30, 2011 (NCEI Accession 0157458). NOAA National Centers for Environmental Information. Dataset. https://accession.nodc.noaa.gov/0157458.

Feely R. A., et al., (2004) Impact of anthropogenic CO2 on the CaCO3 system in the oceans. Science 305, 362-366. doi:10.1126/science.1097329.

Fong M. B. and Dickson A. G. (2019) Insights from GO-SHIP hydrography data into the thermodynamic consistency of CO2 system measurements in seawater. Mar. Chem. 211, 52-63. https://doi.org/10.1016/j.marchem.2019.03.006.

Goyet C. and Poisson A. (1989) New determination of carbonic acid dissociation constants in seawater as a function of temperature and salinity. Deep Sea Res. Part A. Oceanogr. Res. Papers 36, 1635-1654. http://dx.doi.org/10.1016/0198-0149(89)90064-2.

Gruber N., et al., (2019) The oceanic sink for anthropogenic CO2 from 1994 to 2007. Science 363, 1193-1199. doi:10.1126/science.aau5153.

Hansson I. (1973) The determination of the dissociation constants of carbonic acid in synthetic sea water in the salinity range of 20-40‰ and temperature range of 5-30° C. Acta Chem. Scand. 27, 931-944. doi:10.3891/acta.chem.scand.27-0931.

Le Quéré C., et al., (2018) Global carbon budget 2018. Earth Syst. Sci. Data 10, 2141-2194. doi:10.5194/essd-10-2141-2018.

Lee K., Kim T.-W., Byrne R. H., Millero F. J., Feely R. A. and Liu Y.-M. (2010) The universal ratio of boron to chlorinity for the North Pacific and North Atlantic oceans. Geochim. Cosmochim. Acta 74, 1801-1811. https://doi.org/10.1016/j.gca.2009.12.027.

Lee K., Millero F. J., Byrne R. H., Feely R. A. and Wanninkhof R. (2000) The recommended dissociation constants for carbonic acid in seawater. Geophys. Res. Lett. 27, 229-232. doi:10.1029/1999g1002345.

Lee K., Millero F. J. and Campbell D. M. (1996) The reliability of the thermodynamic constants for the dissociation of carbonic acid in seawater. Mar. Chem. 55, 233-245. http://dx.doi.org/10.1016/S0304-4203(96)00064-3.

Liu X., Patsavas M. C. and Byrne R. H. (2011) Purification and characterization of meta-cresol purple for spectrophotometric seawater pH measurements. Environ. Sci. Technol. 45, 4862-4868. doi:10.1021/es200665d.

Lueker T. J., Dickson A. G. and Keeling C. D. (2000) Ocean pCO2 calculated from dissolved inorganic carbon, alkalinity, and equations for K1 and K2: validation based on laboratory measurements of CO2 in gas and seawater at equilibrium. Mar. Chem. 70, 105-119. https://doi.org/10.1016/S0304-4203(00)00022-0.

Dataset]Macdonald A. M., Wanninkhof R., Dickson A. G., Carlson C. A., Key R. M., Becker S., Swift J. H., McNichol A., Schlosser P., and Fripiat F. (2018) Discrete profile measurements of dissolved inorganic carbon, total alkalinity, pH and other hydrographic and chemical data obtained during the R/V Roger Revelle Repeat Hydrography and SOCCOM Cruise in the Indian Ocean and Southern Ocean: GO-SHIP Section I08S, (Expocode 33RR20160208) from Feb. 8, 2016 to Mar. 16, 2016 (NCEI Accession 0171457). NOAA National Centers for Environmental Information. Dataset. https://doi.org/10.7289/v5hm56qr.

Millero F. J. (2010) Carbonate constants for estuarine waters. Mar. Freshw. Res. 61, 139-142. doi:10.1071/MF09254.

Millero F. J., Graham T. B., Huang F., Bustos-Serrano H. and Pierrot D. (2006) Dissociation constants of carbonic acid in seawater as a function of salinity and temperature. Mar. Chem. 100, 80-94. doi:10.1016/j.marchem.2005.12.001.

Millero F. J., Pierrot D., Lee K., Wanninkhof R., Feely R., Sabine C. L., Key R. M. and Takahashi T. (2002) Dissociation constants for carbonic acid determined from field measurements. Deep Sea Res. Part I. Oceanogr. Res. Papers 49, 1705-1723. https://doi.org/10.1016/S0967-0637(02)00093-6.

Mojica Prieto F. J. and Millero F. J. (2002) The values of pK1+pK2 for the dissociation of carbonic acid in seawater. Geochim. Cosmochim. Acta 66, 2529-2540. https://doi.org/10.1016/S0016-7037(02)00855-4.

Müller J. D. and Rehder G. (2018) Metrology of pH measurements in brackish waters—part 2: experimental characterization of purified meta-Cresol Purple for spectrophotometric pHT measurements. Front. Mar. Sci. 5, 1-9. doi:10.3389/fmars.2018.00177.

Orr J. C., Epitalon J.-M., Dickson A. G. and Gattuso J.-P. (2018) Routine uncertainty propagation for the marine carbon dioxide system. Mar. Chem. 207, 84-107. https://doi.org/10.1016/j.marchem.2018.10.006.

Orr J. C et al., (2005) Anthropogenic ocean acidification over the twenty-first century and its impact on calcifying organisms. Nature 437, 681-686. doi:10.1038/nature04095.

Papadimitriou S., Loucaides S., Rérolle V. M. C., Kennedy P., Achterberg E. P., Dickson A. G., Mowlem M. and Kennedy H. (2018) The stoichiometric dissociation constants of carbonic acid in seawater brines from 298 to 267 K. Geochim. Cosmochim. Acta 220, 55-70. https://doi.org/10.1016/j.gca.2017.09.037.

Patsavas M. C., Byrne R. H., Wanninkhof R., Feely R. A. and Cai W.-J. (2015) Internal consistency of marine carbonate system measurements and assessments of aragonite saturation state: Insights from two US coastal cruises. Mar. Chem. 176, 9-20. http://dx.doi.org/10.1016/j.marchem.2015.06.022.

Riebesell U., Zondervan I., Rost B., Tortell P. D., Zeebe R. E. and Morel F. M. (2000) Reduced calcification of marine plankton in response to increased atmospheric CO2. Nature 407, 364-367. doi:https://doi.org/10.1038/35030078.

Roy R. N., Roy L. N., Vogel K. M., Porter-Moore C., Pearson T., Good C. E., Millero F. J. and Campbell D. M. (1993) The dissociation constants of carbonic acid in seawater at salinities 5 to 45 and temperatures 0 to 45° C. Mar. Chem. 44, 249-267. http://dx.doi.org/10.1016/0304-4203(93)90207-5.

Dataset]Swift J. H., Mecking S., Feely R. A., Dickson A. G., Carlson C. A., Jenkins W. J., McNichol A., Key R. M., Ho D. T., Sigman D., Macdonald A. M., Buesseler K., and Martz T. R. (2014) Dissolved inorganic carbon, pH, alkalinity, temperature, salinity and other variables collected from discrete sample and profile observations using CTD, bottle and other instruments from Melville in the North Pacific Ocean and Philippine Sea from Mar. 21, 2013 to May 1, 2013 (NCEI Accession 0117338). NOAA National Centers for Environmental Information. Dataset. https://doi.org/10.3334/cdiac/otg.goship_p02_318m20130321.

Dataset]Talley L. D., Feely R. A., Dickson A. G., Swift J. H., Carlson C. A., Warner M. J., McNichol A., Key R. M., and Schlosser P. (2016) Dissolved inorganic carbon (DIC), total alkalinity, pH on total scale, dissolved organic carbon (DOC), chlorofluorocarbons, temperature, salinity and other hydrographic and chemical variables collected from discrete samples and profile observations during the R/V Nathaniel B. Palmer cruise GO-SHIP_P16S_2014 (Expocode 320620140320) in the South Pacific Ocean from Mar. 20, 2014 to

(56) References Cited

OTHER PUBLICATIONS

May 5, 2014 (NCEI Accession 0157621). NOAA National Centers for Environmental Information. Dataset. https://doi.org/10.3334/cdiac/otg.go_ship_p16s_2014.

Uppström L. R. (1974) The boron/chlorinity ratio of deep-sea water from the Pacific Ocean. Deep Sea Research and Oceanographic Abstracts 21, 161-162. https://doi.org/10.1016/0011-7471(74)90074-6.

Van Heuven S., Pierrot D., Rae J., Lewis E. and Wallace D. (2011) MATLAB program developed for CO2 system calculations. ORNL/CDIAC-105b. Carbon Dioxide Inf. Anal. Cent., Oak Ridge Natl. Lab., US Dept. of Energy, Oak Ridge, Tenn.

Dataset]Wanninkhof R., et al., 2013) Partial pressure (or fugacity) of carbon dioxide, dissolved inorganic carbon, pH, alkalinity, temperature, salinity and other variables collected from discrete sample and profile observations using Alkalinity titrator, CTD and other instruments from Atlantis in the North Atlantic Ocean from Apr. 19, 2012 to May 15, 2012 (NCEI Accession 0108160). NOAA National Centers for Environmental Information. Dataset. https://doi.org/10.3334/cdiac/otg.clivar_a20_2012.

Wanninkhof R., Lewis E., Feely R. A. and Millero F. J. (1999) The optimal carbonate dissociation constants for determining surface water pCO2 from alkalinity and total inorganic carbon. Mar. Chem. 65, 291-301. https://doi.org/10.1016/S0304-4203(99)00021-3.

Dataset]Wanninkhof R., Zhang J.-Z., Baringer M. O., Langdon C., Cai W.-J., Salisbury J. E., and Byrne R. H. (2016) Partial pressure (or fugacity) of carbon dioxide, dissolved inorganic carbon, pH, alkalinity, temperature, salinity and other variables collected from discrete sample and profile observations using CTD, bottle and other instruments from NOAA Ship Ronald H. Brown in the Gray's Reef National Marine Sanctuary, Gulf of Mexico and North Atlantic Ocean from Jul. 21, 2012 to Aug. 13, 2012 (NCEI Accession 0157619). NOAA National Centers for Environmental Information. Dataset. https://doi.org/10.3334/cdiac/otg.coastal_gomecc2.

Waters J. F. and Millero F. J. (2013) The free proton concentration scale for seawater pH. Mar. Chem. 149, 8-22. doi: https://doi.org/10.1016/j.marchem.2012.11.003.

Waters J., Millero F. J. and Woosley R. J. (2014) Corrigendum to "The free proton concentration scale for seawater pH",[MARCHE: 149 (2013) 8-22]. Mar. Chem. 165, 66-67. http://dx.doi.org/10.1016/j.marchem.2012.11.003.

Wittmann A. C. and Pörtner H.-O. (2013) Sensitivities of extant animal taxa to ocean acidification. Nat. Clim. Change 3, 995-1001. doi:10.1038/nclimate1982.

Woosley R. J. (2018) Complexity of marine CO2 system highlighted by seasonal asymmetries. Global Biogeochem. Cycles 32, 1434-1436. doi:10.1029/2018GB006081.

Yao W. and Byrne R. H. (2001) Spectrophotometric determination of freshwater pH using bromocresol purple and phenol red. Environ. Sci. Technol. 35, 1197-1201. https://doi.org/10.1021/es001573e.

Hawley J. E. (1973) Bicarbonate and Carbonate Association with Sodium, Magnesium, and Calcium at 25° C. and 0.72 Ionic Strength. PhD Thesis, Oregon State University, Corvallis. 71 p.

Lewis E., and Wallace D.W.R. (1998) Program developed for CO2 System Calculations. 1020 ORNL/CDIAC-105. Carbon Dioxide Inf. Anal. Cent., Oak Ridge Natl. Lab., U.S. Dept. of Energy, Oak Ridge, Tenn.

Liu, X., Byrne, R.H., Lindemuth, M., Easley, R., and Mathis, J.T. (2015). An automated procedure for laboratory and shipboard spectrophotometric measurements of seawater alkalinity: continuously monitored single-step acid additions. Marine Chemistry. 174: 141-146.

Yang, B., Byrne, R.H., and Lindemuth, M. (2015). Contributions of organic alkalinity to total alkalinity in coastal waters: A spectrophotometric approach. Marine Chemistry. 176: 199-207.

Douglas, N.K. and Byrne, R.H. (2017). Achieving accurate spectrophotometric pH measurements using unpurified meta-cresol purple. Marine Chemistry. 190: 66-72.

Sharp, J.D., Byrne, R.H., Liu, X., Feely, R.A., Cuyler, E.E., Wanninkhof, R., and Alin, S.R. (2017) Spectrophotometric Determination of Carbonate Ion Concentrations: Elimination of Instrument-Dependent Offsets and Calculation of In Situ Saturation States. Environmental Science and Technology, 51: 9127-9136.

Douglas, N.K. and Byrne, R.H. (2017). Spectrophotometric pH measurements from river to sea: Calibration of mCP for 0≤S≤40 and 278.15≤T ≤308.15 K. Marine Chemistry 197: 64-69.

Sharp, Jonathan D., and Robert H. Byrne. "Carbonate ion concentrations in seawater: spectrophotometric determination at ambient temperatures and evaluation of propagated calculation uncertainties." Marine Chemistry 209 (2019): 70-80.

F.J. Millero, D. Pierrot, A chemical equilibrium model for natural waters, Aquat. Geochem. 4 (1998) 153-199.

K.M. Schockman, R.H. Byrne, Spectrophotometric determination of the bicarbonate dissociation constant in seawater, Geochem. Cosmochim. Acta 300 (2021) 231-245.

R.J. Woosley, Evaluation of the temperature dependence of dissociation constants for the marine carbon system using pH and certified reference materials, Mar. Chem. 229 (2021), 103914.

G.N. Lewis, M. Randall, The activity coefficient of strong electrolytes, J. Am. Chem. Soc. 43 (1921) 1112-1154.

P. Debye, E. Hückel, Zur theorie der elektrolyte. I. Gefrierpunktserniedrigung und verwandte erscheinunge (The theory of electrolytes. I. Lowering of freezing point and related phenomena), Phys. Z. 24 (1923) 185-206.

U.S. Geological Survey, Specific Conductance: USGS Techniques and Methods, Book 9, Ch. A6.3, 2019, p. 15 [Supersedes USGS Techniques of Water-Resources Investigations, Book 9, Ch. A6.3, v1.2. 24 pages.

D.A. Livingstone, Chemical composition of rivers and lakes, Professional Paper, USGS Numbered Series, 1963, 440-G. 75 pages.

F.T. Mackenzie, R.M. Garrels, Chemical mass balance between rivers and oceans, Am. J. Sci. 264 (1966) 507.

G.L. Robert-Baldo, M.J. Morris, R.H. Byrne, Spectrophotometric determination of seawater pH using phenol red, Anal. Chem. 57 (1985) 2564-2567.

YSI, Professional 30 (Pro30) Handheld Conductivity Meter, User Manual, Author, Yellow Springs, OH, 2011.

Guildline Instruments, Model 8400B Autosal Laboratory Salinometer, Technical Manual, Author, Smith Falls, ON, Canada, 2004.

S. Markich, P. Brown, Relative importance of natural and anthropogenic influences on the fresh surface water chemistry of the Hawkesbury-Nepean River, southeastern Australia, Sci. Total Environ. 217 (1998) 201-230.

L.A. Pillsbury, Spatial and temporal chemical variations in the Hillsborough river system, University of South Florida, USF Graduate Theses and Dissertations, 2004.

F.J. Millero, D.R. Schreiber, Use of the ion pairing model to estimate activity coefficients of the ionic components of natural waters, Am. J. Sci. 282 (1982) 1508-1540.

G.M. Marion, K.L. Babcock, Predicting specific conductance and salt concentration in dilute aqueous solutions, Soil Sci. 122 (1976) 181.

A.G. Dickson, C.L. Sabine, J.R. Christian (Eds.), Guide to Best Practices for Ocean CO2 Measurements, vol. 3, PICES Special Publication, 2007, p. 191.

T.D. Clayton, R.H. Byrne, J.A. Breland, R.A. Feely, F.J. Millero, D.M. Campbell, P. P. Murphy, M.F. Lamb, The role of pH measurements in modern oceanic CO2-system characterizations: precision and thermodynamic consistency, Deep Sea Res. Part II Top. Stud. Oceanogr. 42 (1995) 411-429.1.

J.D. Naviaux, A.V. Subhas, S. Dong, N.E. Rollins, X. Liu, R.H. Byrne, W.M. Berelson, J.F. Adkins, Calcite dissolution rates in seawater: lab vs. in-situ measurements and inhibition by organic matter, Mar. Chem. 215 (2019), 103684.

* cited by examiner ns,710 B2

METHODS AND SYSTEMS FOR DETERMINING AN IONIC STRENGTH OF A DILUTE AQUEOUS SOLUTION

CROSS-REFERENCE TO RELATED APPLICATION

This application claims benefit of U.S. Provisional Application No. 63/043,885 filed Jun. 25, 2020, the content of which is hereby incorporated herein by reference in its entirety.

BACKGROUND

The ionic composition of river water determines its effect on the aquatic ecosystem surrounding the rivers and oceans that the rivers stream to. The ionic composition of river water also can affect the interactions of various nutrients and pollutants alike and, therefore, to determine its use for human and animal consumption and various industries.

It is understood that human needs, aquatic animals' needs, irrigation, or agricultural needs require a different extent of water quality. Therefore, to understand the behavior of pollutants and nutrients in the river water, it is also important to know the ionic strength of river water that is dependent on water composition. More specifically, the solubility and dissociation of various salts present in the water are dependent on a total concentration of ions present in this solution.

The ionic strength of natural water sources such as lakes and rivers, which have a dilute concentration of various ions, cannot currently be directly measured. The ionic strength of such dilute solutions needs to be known to calculate and model the behaviors of dissolved substances (pollutants, carbon dioxide absorption, nutrients, trace metals, etc.). In certain solutions, such as seawater, the relative concentrations of major dissolved ions are substantially constant, allowing ionic strength to be determined through measurements of conductivity and conductivity ratios.

However, in natural freshwaters, the relative concentrations of ions are highly variable (due to the changes in ground erosion, rains, seasonal changes, human activity, etc.) and, therefore, conductivity measurements to determine ionic strength of river and lake waters are highly unreliable.

Thus, there is a need for methods and systems, allowing the determination of ionic strength of the diluted aqueous solutions that are reliable and portable. These needs and other needs are at least partially satisfied by the present disclosure.

SUMMARY

The present invention is directed to a method comprising n stages for determining an ionic strength I of an aqueous sample, wherein the method comprises: a first of the n stages comprising: a) adding a pH indicator to a portion of the aqueous sample; b) adjusting a pH of the portion of the aqueous sample to obtain a $pH_{initial}$ value; c) adding an amount of a buffer to the portion of the aqueous sample to obtain a $pH_{final}$; d) repeating steps a)-c) for n times, until $pH_{initial}$ is substantially similar to a $pH_{final}$, and is defined as an equilibrium $pH^0$, and wherein a portion of the aqueous sample in step a) of each subsequent stage is a new portion of the aqueous sample; and a $pH_{initial}$ in step b) of each subsequent stage is different from a $pH_{initial}$ of each preceding stage; and e) calculating the I value from a ratio of a total alkalinity of the aqueous sample to a total concentration of the buffer $A_t/[Buffer]_t$, wherein the I value is calculated as a function of a specific dissociation constant of the buffer, and wherein a temperature of the portion of the aqueous sample at steps b) and c) is substantially identical.

Still further disclosed herein is a method for determining an ionic strength I of an aqueous sample, wherein the method comprises a) measuring a pH of the aqueous sample, wherein the aqueous sample comprises a pH indicator to obtain a $pH_1$ value of the aqueous sample; b) adding a first volume of a first buffer solution to the aqueous sample to arrive at $pH_2$, wherein the $pH_2$ is smaller or higher than $pH_1$; c) adding a second volume of a second buffer solution to the aqueous sample to arrive at $pH_3$, wherein the $pH_3$ is substantially identical to the $pH_1$; d) determining the I value from a ratio of a total alkalinity of the aqueous sample to a total concentration of the buffer $A_t/[Buffer]_t$, wherein the ratio $A_t/[Buffer]_t$ is provided by a ratio of the first volume and the second volume of the first and the second buffer solutions and by a composition of the first and the second buffer solutions, and wherein the I value is calculated as a function of a specific dissociation constant of the buffer; wherein a temperature of the aqueous sample at steps a) through c) is substantially identical; and wherein the first and the second volumes of the first and second buffer solution do not substantially change the I value of the aqueous sample.

In still further aspects, the $pH_{initial}$ and/or $pH_{final}$ in disclosed herein methods are measured spectroscopically.

Still further disclosed herein is a system for measuring an ionic strength of an aqueous sample comprising: a) a device comprising) a spectrophotometer; and ii) at least one optical cell configured to obtain a portion of the aqueous sample, wherein the portion of the aqueous sample has a predetermined volume; b) a first dispenser configured to add an amount of an acid or a base to the portion of the aqueous sample to obtain a $pH_{initial}$ value; and c) a second dispenser configured to add an amount of a buffer to the portion of the aqueous sample to obtain a $pH_{final}$.

Also disclosed herein is a system for measuring an ionic strength of an aqueous sample comprising: a) a device comprising i) a spectrophotometer; and ii) at least one optical cell configured to obtain the aqueous sample comprising a pH indicator and to measure a $pH_1$ value of the aqueous sample; b) a first dispenser configured to add a first volume of a first buffer solution to obtain a $pH_2$ value of the aqueous sample, wherein the $pH_2$ is lower or higher than $pH_1$, and c) a second dispenser configured to add a second volume of a second buffer solution to obtain a $pH_3$ value of the aqueous sample, wherein the $pH_3$ is substantially equal to $pH_1$.

In yet further aspects, the systems disclosed herein are portable. While yet, in other aspects, the systems disclosed herein are automatic.

Additional aspects of the disclosure will be set forth, in part, in the detailed description, FIGURES, and claims which follow, and in part will be derived from the detailed description, or can be learned by practice of the invention. It is to be understood that both the foregoing general description and the following detailed description are exemplary and explanatory only and are not restrictive of the invention as disclosed.

DETAILED DESCRIPTION

The present invention can be understood more readily by reference to the following detailed description, examples, drawings, and claims, and their previous and following description. However, before the present articles, systems, and/or methods are disclosed and described, it is to be understood that this invention is not limited to the specific or exemplary aspects of articles, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein while still obtaining the beneficial results of the present invention. It will also be apparent that some of the desired benefits of the present invention can be obtained by selecting some of the features of the present invention without utilizing other features. Accordingly, those of ordinary skill in the pertinent art will recognize that many modifications and adaptations to the present invention are possible and may even be desirable in certain circumstances and are a part of the present invention. Thus, the following description is again provided as illustrative of the principles of the present invention and not in limitation thereof.

Definitions

As used herein, the singular forms "a," "an," and "the" include plural referents unless the context clearly dictates otherwise. Thus, for example, reference to a "portion" includes aspects having two or more such portions unless the context clearly indicates otherwise.

It is appreciated that certain features of the disclosure, which are, for clarity, described in the context of separate aspects, can also be provided in combination in a single aspect. Conversely, various features of the disclosure, which are, for brevity, described in the context of a single aspect, can also be provided separately or in any suitable subcombination.

As used herein, the terms "optional" or "optionally" mean that the subsequently described event or circumstance may or may not occur, and that the description includes instances where said event or circumstance occurs and instances where it does not.

It is also to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this invention belongs. In this specification and in the claims, which follow, reference will be made to a number of terms that shall be defined herein.

For the terms "for example" and "such as," and grammatical equivalences thereof, the phrase "and without limitation" is understood to follow unless explicitly stated otherwise.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value and/or to "about" another particular value. When such a range is expressed, another aspect includes from the one particular value and/or to the other particular value.

Similarly, when values are expressed as approximations, by use of the antecedent "about," it will be understood that the particular value forms another aspect. It will be further understood that the endpoints of each of the ranges are significant both in relation to the other endpoint and independently of the other endpoint. Unless stated otherwise, the term "about" means within 5% (e.g., within 2% or 1%) of the particular value modified by the term "about."

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6 and any whole and partial increments therebetween. This applies regardless of the breadth of the range.

As used herein, the term "composition" is intended to encompass a product comprising the specified ingredients in the specified amounts, as well as any product which results, directly or indirectly, from a combination of the specified ingredients in the specified amounts. In yet further aspects, and as described herein, the term "composition" can also refer to a product whose exact components are known and are determined by the methods disclosed herein.

As used herein, the term "substantially," in, for example, the context "substantially no change" refers to a phenomenon or an event that exhibits less than about 1% change, e.g., less than about 0.5%, less than about 0.1%, less than about 0.05%, or less than about 0.01% change. For example, when the term substantially no change is used in the context of substantially no change is observed in the oscillations of the molten electrolyte, it is understood that the change in the oscillations is less than about 1%, less than about 0.5%, less than about 0.1%, less than about 0.05%, or less than about 0.01%.

As used herein, the term "substantially," in, for example, the context "substantially identical" or "substantially similar" refers to a method or a system, or a component that is at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by similar to the method, system, or the component it is compared to.

As used herein, the term "ionic strength" refers to a measure of the concentration of ions that are present in the solution that can be expressed as:

$$I = \tfrac{1}{2} \sum_{i=1}^{n} c_i z_i^2;$$

where $c_i$ is a molar concentration of ion i and $z_i$ is a charge number of that ion.

As used herein, the terms a "buffer" or a "pH buffer" are used interchangeably and refer to an aqueous solution comprising a mixture of a weak acid and its conjugate base, or vice versa and is known to resist a pH change in response to a small addition of strong acid or base.

While aspects of the present invention can be described and claimed in a particular statutory class, such as the system statutory class, this is for convenience only and one of ordinary skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred in any respect. This holds for any possible non-express basis for interpretation, including matters of logic with respect to arrangement of steps or operational flow, plain meaning derived from grammatical organization or punctuation, or the number or type of aspects described in the specification.

The present invention may be understood more readily by reference to the following detailed description of various aspects of the invention and the examples included therein and to the Figures and their previous and following description.

Methods

The present disclosure provides a method comprising n stages for determining an ionic strength I of an aqueous sample, wherein the method comprises: a first of the n stages comprising: a) adding a pH indicator to a portion of the aqueous sample; b) adjusting a pH of the portion of the aqueous sample to obtain a $pH_{initial}$ value; c) adding an amount of a buffer to the portion of the aqueous sample to obtain a $pH_{final}$; d) repeating steps a)-c) for n times, until $pH_{initial}$ is substantially similar to a $pH_{final}$, and is defined as an equilibrium $pH^0$, and wherein a portion of the aqueous sample in step a) of each subsequent stage is a new portion of the aqueous sample; and a $pH_{initial}$ in step b) of each subsequent stage is different from a $pH_{initial}$ of each preceding stage; and e) calculating the I value from a ratio of a total alkalinity of the aqueous sample to a total concentration of the buffer $A_t/[Buffer]_t$, wherein the I value is calculated as a function of a specific dissociation constant of the buffer; and wherein a temperature of the portion of the aqueous sample at steps b) and c) is substantially identical.

It is understood that the aqueous samples disclosed herein can be any samples whose ionic strength needs to be determined. In certain aspects, the aqueous samples, as disclosed herein, have a low ionic strength. In still further aspects, the aqueous samples can comprise river water, lake water, or any combination thereof. It is understood that the ionic strength of the solution can affect the dissolution of various nutrients and contaminants within the solution. It is known that the precipitation constant or dissociation constant of various components can be strongly dependent on the ionic strength of the solution. It is also understood that without knowing the precise composition of the solution, it is challenging to determine its ionic strength with the desired precision and accuracy. Thus, the methods disclosed herein overcome those challenges.

In certain aspects, it is understood that the initial pH of the aqueous solution can be any pH. While in other exemplary aspects, where the aqueous sample comprises a river or lake water, the pH of such an aqueous solution can be slightly acidic or slightly basic. In still further aspects, the initial pH can be from about 6 to about 9, including exemplary values of about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0 about 8.1, about 8.2, about 8.3, about 8.4, about 8.5, about 8.6, about 8.7, about 8.8, and about 8.9. In yet still further aspects, the initial pH can have a value between any two foregoing values.

The methods described herein comprise n stages needed to precisely determine an ionic strength of the aqueous sample.

In certain aspects, the pH indicator added at any stage of the n stages can be any indicator known in the art that changes its characteristics with a change in pH. For example, in certain aspects, the pH indicator is an indicator that changes its color as a function of the pH change. In such exemplary aspects, the change in pH can be measured spectroscopically. In yet further aspects, the pH indicator can have a color transition at the desired pH.

In still further aspects, any pHs that are described herein are measured spectroscopically. In such exemplary aspects and as disclosed above, the pH indicator can comprise any indicator that has at least two dissociation constants and has a monoprotonated form $HIN^-$ and a fully protonated form $IN^{2-}$. In still further exemplary and unlimiting aspects, the pH indicator can comprise a substantially purified sulfonephthalein, bromocresol purple, m-cresol purple, phenylphenol, or thymol blue, bromothymol blue, or chlorophenol red.

In yet further aspects, a pH of the portion of the aqueous sample can be adjusted with an acid or a base to achieve a $pH_{initial}$ that is substantially near an expected equilibrium $pH^0$ appropriate to the sample's temperature.

In still further aspects, the expected equilibrium $pH^0$ can be anywhere between about 6 and about 8, including exemplary values of about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0 about 8.1, about 8.2, about 8.3, about 8.4, about 8.5, about 8.6, about 8.7, about 8.8, and about 8.9 and a temperature between about 15° C. and about 35° C., including exemplary values of about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., and about 34° C.

In such exemplary aspects, the acid can comprise any strong acid, such as, for example, HCl, $H_2SO_4$, or $HNO_3$. In yet further aspects, the base can comprise any strong base, such as NaOH or KOH. It is understood, however, when the acid or the base are used to adjust the pH of the portion of the aqueous sample, they are added in an amount that is not expected substantially to change the ionic strength of the aqueous sample. In other words, step c) of adjusting the pH of the method described herein comprises adding an amount of an acid or a base, wherein the amount of the acid or base is effective to introduce substantially no change to the I value of the aqueous sample.

In still further aspects, the method further comprises adding an amount of a buffer to the portion of the aqueous sample to obtain a $pH_{final}$. It is understood that the buffer solution can be added as a solid or as a solution in any amount that does not substantially affect the ionic strengths of the portion of the aqueous sample. In still further aspects, the buffer is purified prior to use.

In still further aspects, the steps a) through c) of the methods disclosed herein are repeated for n times until $pH_{initial}$ is substantially similar to a $pH_{final}$, and is defined as an equilibrium $pH^0$.

It is understood that in the methods disclosed herein, a portion of the aqueous sample in step a) of each subsequent stage is a new portion of the aqueous sample. In still further aspects, a $pH_{initial}$ in step b) of each subsequent stage can be different from a $pH_{initial}$ of each preceding stage. Yet in further aspects, the methods described herein comprises steps of calculating the I value from a ratio of a total alkalinity of the aqueous sample to a total concentration of the buffer $A_t/[Buffer]_t$, wherein the I value is calculated as a function of a specific dissociation constant K of the buffer. In certain aspects, the buffers can be polyprotic. In such exemplary aspects, the buffer can have two or more specific dissociation constants. It is understood that a temperature of the portion of the aqueous sample at steps b) and c) is kept substantially identical.

In still further aspects, it is understood that the specific dissociation constant (constants) K of the buffer is dependent on a type of buffer. For example, in certain aspects, when the buffer is monoprotonated, the buffer has only one specific dissociation constant. In yet other aspects, when the buffer comprises the diprotic or polyprotic system, the buffer is defined by two or more specific dissociation constants describing each specific deprotonation step.

It is further understood that the dependence of the specific dissociation constant from the ionic strength can be determined based on the Debye-Hückel theorem and can be expressed according to Equation (1):

$$\log_{10} K = A*I^{0.5}/(1+B*I^{0.5}) + D*I + C \qquad (1).$$

It is understood that A is a constant calculated according to an equation Debye-Hückel equation and can be expressed as Equation (2):

$$A = \frac{1.83 \times 10^6 \, \rho^{1/2}}{(\varepsilon T)^{3/2}} \Delta z^2, \qquad (2)$$

wherein $$\Delta z^2 = \Sigma \Delta z_{i(products)}^2 - \Sigma \Delta z_{i(reactants)}^2 \qquad (3),$$

and wherein a $z_i$ is a charge number of the species present in the sample.

It is further understood that B is a constant that can also be calculated according to the Debye-Hückel Equation and can be expressed as Equation (4):

$$B = \frac{50.29 \times 10^6 \, \rho^{1/2}}{(\varepsilon T)^{1/2}} \alpha; \qquad (4)$$

wherein ρ and ε are density and dialectic constants of the water, respectively, at the temperature of the portion, and α is a size of a buffer ion in cm. It is understood that these constant are known in the art and can be found in the literature. In yet other aspects, B can be found semi-empirically or can be determined by linear fitting of Equation (1). In yet further aspects, the values of the constants in the Debye-Hückel Equation can be found according to methods disclosed by G. G. Manov et al. JACS, 1943, 65, 9, 1765-1767, the content of which is incorporated herein by reference.

In still further aspects, the constant D can be a fitting parameter of Equation (1).

In still further aspects, C is $\log_{10} K^0$, and wherein $K^0$ is a specific equilibrium coefficient of the buffer in pure water having I=0 or wherein C is an intercept with axis y.

In yet further aspects, it is understood that the buffer can be any buffer known in the art. In yet other aspects, the buffer can comprise a mixture of various buffers. Without wishing to be bound by any theory, it is understood that the composition of the buffer needs to be known in order to calculate the specific dissociation characteristics of the chosen buffer. In still further exemplary aspects, the buffer can comprise one or more of a bicarbonate buffer, a phosphate buffer, or a borate buffer.

In yet further exemplary aspects, the dissociation equations of the buffers can be presented as follows. For example, when the buffer used in the methods disclosed herein is bicarbonate, its dissociation can be determined according to the following reactions:

$$H_2CO_3 \leftrightarrow HCO_3^- + H^+; \qquad (a)$$

$$pH = pK_1 + \log\frac{[HCO_3^-]}{[H_2CO_3]}; \Delta z^2 = 2;$$

wherein

$$\log_{10} K_1 = \log_{10} K_1^0 + \frac{1.02 I^{1/2}}{1 + B_1 I^{1/2}} + D_1 I \qquad (b)$$

$$HCO_3^- \leftrightarrow CO_3^{2-} + H^+; pH = pK_2 + \log\frac{[CO_3^{2-}]}{[HCO_3^-]}; \Delta z^2 = 4;$$

and wherein $$\log_{10} K_2 = \log_{10} K_2^0 + \frac{2.044 I^{1/2}}{1 + B_2 I^{1/2}} + D_2 I,$$

wherein $K_1^0$ and $K_2^0$ are dissociation constants of the carbonic acid and the bicarbonate at an ionic strength equal to zero. These constants can also be found as an intercept with a y-axis from Equation (1).

In yet other exemplary aspects, where the buffer is a borate buffer, its dissociation can be determined according to the following reaction:

$$B(OH)_3 + H_2O \leftrightarrow B(OH)_4^- + H^+; \qquad (c)$$

$$pH = pK_2 + \log\frac{[B(OH)_4^-]}{[B(OH)_3]}; \Delta z^2 = 2;$$

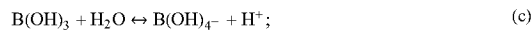

$$\text{wherein } \log_{10} K_B = \log_{10} K_B^0 + \frac{1.02 I^{1/2}}{1 + B_B I^{1/2}} + D_B I$$

In yet other exemplary aspects, where the buffer is a phosphate buffer, its dissociation can be determined according to the following reactions:

$$H_3PO_4 \leftrightarrow H_2PO_4^- + H^+; pH = pK_1 + \log\frac{[H_2PO_4^-]}{[H_3PO_4]}; \Delta z^2 = 2; \qquad (d)$$

wherein $$\log_{10} K_1 = \log_{10} K_1^0 + \frac{1.02 I^{1/2}}{1 + B_2 I^{1/2}} + D_1 I$$

$$H_2PO_4^- \leftrightarrow HPO_4^{2-} + H^+; pH = pK_2 + \log\frac{[HPO_4^{2-}]}{[H_2PO_4^-]}; \Delta z^2 = 4; \quad (e)$$

wherein $$\log_{10} K_2 = \log_{10} K_2^0 + \frac{2.044 I^{1/2}}{1 + B_2 I^{1/2}} + D_2 I$$

$$HPO_4^{2-} \leftrightarrow PO_4^{3-} + H^+; pH = pK_3 + \log\frac{[PO_4^{3-}]}{[HPO_4^{2-}]}; \Delta z^2 = 6; \quad (f)$$

wherein $$\log_{10} K_3 = \log_{10} K_3^0 + \frac{3.066 I^{1/2}}{1 + B_3 I^{1/2}} + D_3 I$$

In yet further aspects, the appropriate K values of the buffers used herein can be extrapolated from the Equation disclosed above based on the data provided in the literature. For example, and without limitation, the values can be extrapolated from the data shown by K. J. Powell et al. in Pure Appl. Chem. Vol. 77, No. 4, pp. 739-800, 2005, the content of which is incorporated herein by reference.

In still further aspects, the ratio of $A_t/[Buffer]_t$ can be expressed using K values disclosed above.

In yet other aspects, wherein the buffer is the bicarbonate buffer $A_t/[Buffer]_t$ is according to Equation (5):

$$\frac{A_t}{[Buffer]_t} = \frac{2K_1 K_2 + K_1 \left[10^{-pH^0}\right]}{K_1 K_2 + K_1 \left[10^{-pH^0}\right] + \left[10^{-2pH^0}\right]} = 1 \quad (5)$$

wherein $K_1$ and $K_2$ are dissociation constant of bicarbonate expressed according to Equation (1) or more particularly according to equations (a) and (b) as shown above. In still further aspects, the ionic strength value can be mathematically calculated from the disclosed above equations.

In yet other aspects, wherein the buffer is the borate buffer $A_t/[Buffer]_t$ is according to Equation (6):

$$\frac{A_t}{[Buffer]_t} = \frac{K_{borate}}{K_{borate} + \left[10^{-pH^0}\right]} = \frac{1}{2}; \quad (6)$$

wherein $K_{borate}$ is a dissociation constant of borate buffer expressed according to Equation (1) or, more particularly, Equation (c), as shown above. In still further aspects, the ionic strength value can be mathematically calculated from the disclosed above equations.

In yet other aspects, wherein the buffer is the phosphate buffer $A_t/[Buffer]_t$ is according to Equation (7):

$$\frac{A_t}{[Buffer]_t} = \frac{2K_1 K_2 K_3 + K_1 K_2 \left[10^{-pH^0}\right]}{K_1 K_2 K_3 + K_1 K_2 \left[10^{-pH^0}\right] + K_1 \left[10^{-pH^0}\right] + \left[10^{-3pH^0}\right]} =, \quad (7)$$

wherein 0≤X≤2 and a function of a concentration ratio of $H_2PO_4^-$ and $HPO_4^{2-}$. In such aspects, X can be 0, 0.5, 1, 1.5, or 2. It is also understood that X can have any value between any two foregoing values depending on the concentration of $H_2PO_4^-$ and $HPO_4^{2-}$ species. In still further aspects, wherein the buffer comprises $Na_2HPO_4$ a $KH_2PO_4$, for example, Equation (7) can be re-written in a more simplified form as Equation (7'):

$$\frac{A_t}{[Buffer]_t} = \frac{2K_2 K_3 + K_2 \left[10^{-pH^0}\right]}{K_2 K_3 + K_2 \left[10^{-pH^0}\right] + \left[10^{-2pH^0}\right]} = X, \quad (7')$$

In still further aspects, each portion in each of the n stages has a substantially similar volume.

In yet further aspects, the methods described herein further comprise determining a $pH_{initial'}$ having a lowest value of $pH_{initial}$ values measured at each of n stages, for which adding the amount of buffer in step d) provides for a $pH_{final'}$ value that is lower than the $pH_{initial'}$. It is understood that as described herein, the lowest $pH_{initial'}$ refers to an observation that if the $pH_{initial}$ has a value lower than $pH_{initial'}$, the $pH_{final}$ starts to increase instead of decreasing.

In yet further aspects, the methods further comprise determining a $pH_{initial''}$ having a highest value of $pH_{initial}$ values measured at each of n stages, for which adding the amount of buffer in step d) provides for a $pH_{final''}$ value that is higher than a $pH_{initial''}$. It is understood that as described herein, the highest $pH_{initial''}$ refers to an observation that if the $pH_{initial}$ has a value higher than $pH_{initial''}$, the $pH_{final}$ starts to decrease instead of increasing.

In still further aspects, the method further comprising calculating a $pH^0_{i(avg)}$, wherein the $pH^0_{i(avg)}$ is an average of the $pH_{initial'}$ and $pH_{initial''}$. In yet further aspects, the method further comprises calculating a $pH^0_{t(avg)}$, wherein the $pH^0_{t(avg)}$ is an average of the $pH_{final'}$ and $pH_{final''}$. It is understood that in the aspects of the described method, the temperature of the aqueous sample at steps c) and d) of each subsequent stage can be the same or different. Yet, in other aspects, the temperature of the aqueous sample at steps c) and d) of each subsequent stage is controlled and recorded.

In yet further aspects, the methods disclosed herein comprise n repetitions of the disclosed steps, the $pH^0_{i(avg)}$ is substantially identical to the $pH^0_{t(avg)}$. In such aspects, the substantially identical can be any wherein between ±0.01 to less than ±0.001, including any values between any two foregoing values, for example, and without limitations ±0.01, ±0.009, ±0.008, ±0.007, ±0.006, ±0.005, ±0.004, ±0.003, ±0.002, or ±0.001.

It is further understood that pH indicators used in the methods disclosed herein are weak bases and/or weak acids. In such aspects, the dissociation constant of such pH indicators is also dependent on the ionic strength of the aqueous sample. In still further aspects, to more precisely measure the pH of the aqueous sample as a function of the color change of the pH indicator, the measured pH needs to be corrected to encounter the dependence of the dissociation constant of the indicator on the ionic strength of the aqueous sample.

Some quantitative principles of spectrophotometric pH measurements have been described in a variety of previous works (Byrne, R. H.; Breland, J. A. Deep-Sea Res. Part A 1989, 36, 803: Clayton, T. D.; Byrne. R. H. Deep-Sea Res. Part A 1993, 40, 2115; Zhang, H.; Byrne, R. H. Mar. Chem. 1996, 52, 17) and U.S. Patent Application Publication No. 2006/0234388 and U.S. Pat. No. 5,9205,572, the contents of which are incorporated herein in their whole entirety.

In certain exemplary aspects, the indicators denoted as $H_2IN$ can exist in solution in a monoprotic form $HIN^-$ and fully dissociated deprotonated form $IN_2^-$.

In certain aspects, the $pH_{initial}$ and/or $pH_{final}$ is measured according to Equation (8):

$$pH' = -_{IN}(\log(K_2^{IN}e_2)) + \log((R-e_1)/(1-Re_4)) \quad (8);$$

wherein pH' is the $pH_{initial}$ and/or $pH_{final}$ of the aqueous sample; $K_2^{IN}$ is an equilibrium constant for a second dissociation step of the pH indicator. In still further aspects, R is $A_{\lambda_2}/A_{\lambda_1}$; wherein is A, and $A_{\lambda_2}$ are indicator absorbances at $\lambda_1$ and $\lambda_2$ respectively, wherein $\lambda_1$ is a wavelength of absorbance maxima for $HIN^-$ and $\lambda_2$ is a wavelength of absorbance maxima for $IN^{2-}$. In yet further aspects, $e_1$, $e_2$, $e_3$, and $e_4$ are ratios of molar absorptivity coefficients expressed according to:

$$e_1 = _{\lambda_2}\varepsilon_{HIN^-}/_{\lambda_1}\varepsilon_{HIN^-}$$

$$e_2 = _{\lambda_2}\varepsilon_{IN^{2-}}/_{\lambda_1}\varepsilon_{HIN^-}$$

$$e_3 = _{\lambda_2}\varepsilon_{IN^{2-}}/_{\lambda_1}\varepsilon_{HIN^-}$$

$$e_4 = e_3/e_2 = _{\lambda_2}\varepsilon_{IN^{2-}}/_{\lambda_1}\varepsilon_{IN^{2-}}$$

and wherein $\varepsilon$ is a molar absorptivity coefficient of a monoprotonated form of the indicator $HIN^-$ or a fully deprotonated form of the indicator $IN^{2-}$ at $\lambda_2$ and $\lambda_1$, respectively. In still further aspects, in order to estimate a possible change, $_{IN}(\log(K_2^{IN}e_2))$ is determined semi-empirically as a function of the ionic strength and temperature of the aqueous solution. In such aspects, the semi-empirical estimation can be done by conductivity measurements. It is understood that while the conductivity measurements cannot provide for a precise measurement of the ionic strength, and therefore it needs to be calculated based on the equations presented herein, it can provide an estimate useful for the disclosed above correction. In still further aspects, when the ionic strength is measured for the seawater, the calibration of the indictors can be done using seawater conductivity RATIOS and provide a more precise calibration.

In yet other aspects and as disclosed above, the pH indicator can be any indicator known in the art that is configured to change its color as a function of the pH. In certain exemplary aspects, wherein the pH indicator is thymol blue, the $_{IN}(\log(K_2^{IN}e_2))$ is estimated according to Equation (9):

$$_{IN}(\log(K_2^{IN}e_2)) = \quad (9)$$
$$A + BS_p^{0.5}T + CT^{-0.5}S_p + \frac{D}{T} + ES_p + FS_p^{1.5} + GS_p^2 + HS_p^{2.5}$$

wherein $S_p$ is a salinity of the aqueous sample that is linearly dependent on the ionic strength of the aqueous solution and T is a temperature of the aqueous sample; and wherein A, B, C, D, F, G, and H are parameters that are found in the art (E. Hudson-Heck et al. Analytica Chimica Acta, 1090 (2019), 91-99, the content of which is incorporated herein by reference) or are fitting parameters of Equation (9). The optical parameters of thymol blue can be measured at $\lambda_2=596$ nm and $\lambda_1=432$ nm. Again, as disclosed in the preceding aspects, the ionic strength for estimation of $S_p$ (for sweater) can be measured by conductivity measurements.

In still further aspects, for river waters, pH can also be measured using phenol red or bromocresol purple according to the Equation (10) and as described in the U.S. Patent Application Publication No. 2006/0234388, the content of which is incorporated herein in its whole entirety:

$$pH' = pK_1 + \log\frac{(R-e_1)}{(e_2-Re_3)} - 4A\left(\frac{I^{1/2}}{1+I^{1/2}} - 0.3I\right); \quad (10)$$

wherein I is the ionic strength, and A is $A=0.5115+(T-298.15)\times8.57\times10^{-4}$.

In such exemplary and unlimiting aspects, the final terms in Equation (10) account for the variation of $I^{2-}$, $HI^-$, and $H^+$ activity coefficients with ionic strength using the Davies equation. In still further aspects, the ionic strength can be approximately measured by conductivity measurements. The optical parameters of phenol red can be measured at $\lambda_2=558$ nm and $\lambda_1=433$, where $$pK_1^0 \text{ (phenol red)} = 5.798 + \frac{666.7}{T}$$

For the indicator bromocresol purple, the optical parameters can be measured at $\lambda_2=589$ nm and $\lambda_1=432$ nm, where $$pK_1^0 \text{ (bromcresol purple)} = 5.226 + \frac{378.1}{T}$$

In still further aspects, the volume of the portion of the aqueous sample is from about 1 mL to about 30 mL, including exemplary values of about 2 mL, about 5 mL, about 10 mL, about 15 mL, about 20 mL, and about 25 mL.

In still further aspects, the temperature of the portion can be controlled by any known in the art methods. For example, and without limitation, using a water or oil temperature bath, or use of a temperature jacket, or any other method that ensures precise control of the temperature.

In still further aspects, also disclosed herein is a method for determining an ionic strength I of an aqueous sample, wherein the method comprises: a) measuring a pH of the aqueous sample, wherein the aqueous sample comprises a pH indicator to obtain a $pH_1$ value of the aqueous sample; b) adding a first volume of a first buffer solution to the aqueous sample to arrive at $pH_2$, wherein the $pH_2$ is smaller or higher than $pH_1$; c) adding a second volume of a second buffer solution to the aqueous sample to arrive at $pH_3$, wherein the $pH_3$ is substantially identical to the $pH_1$; and d) determining the I value from a ratio of a total alkalinity of the aqueous sample to a total concentration of the buffer $A_t/[Buffer]_t$, wherein the ratio $A_t/[Buffer]_t$ is provided by a ratio of the first volume and the second volume of the first and the second buffer solutions and by a composition of the first and the second buffer solutions, and wherein the I value is calculated as a function of a specific dissociation constant of the buffer; wherein a temperature of the aqueous sample at steps a) through c) is substantially identical; and wherein the first and the second volumes of the first and second buffer solution do not substantially change the I value of the aqueous sample.

In such aspects, any of the disclosed above equations can be used to measure a dissociation constant of the buffer and/or indicator.

In still further aspects, the first buffer solution and/or the second buffer solution comprises one or more of a bicarbonate buffer, a phosphate buffer, or a borate buffer. In yet in some exemplary aspects, the first buffer solution can comprise $NaH_2PO_4$. While in other exemplary aspects, the second buffer solution can comprise $K_2HPO_4$.

In still further aspects, the $A_t/[Buffer]_t$ ratio can be calculated according to any disclosed above equations. In yet further aspects, the pH can be corrected for the indicator's dependence on the ionic strength according to any of the disclosed above equations.

In yet further aspects, also described herein methods where for a natural aqueous solution, a buffer with a well-defined composition can be added to the aqueous solution, without substantially changing the pH of the solution. In such aspects, finding the appropriate pH and the appropriate buffer composition can require iterative adjustments to the solution and/or the buffer. In such exemplary aspects, one of ordinary skill in the art based on a knowledge of (a) the invariant solution pH, (b) the buffer composition that results in no pH change, (c) the influence of ionic strength on the buffer's dissociation constants and (d) the influence of ionic strength on the physical-chemical properties of a spectrophotometric pH indicator, can solve the physical/chemical equations describing the system for the ionic strength of the original natural solution.

Systems

Also disclosed herein is a system for measuring an ionic strength of an aqueous sample comprising: a) a device comprising i) a spectrophotometer; and ii) at least one optical cell configured to obtain a portion of the aqueous sample, wherein the portion of the aqueous sample has a predetermined volume; b) a first dispenser configured to add an amount of an acid or a base to the portion of the aqueous sample to obtain a $pH_{initial}$ value; and c) a second dispenser configured to add an amount of a buffer to the portion of the aqueous sample to obtain a $pH_{final}$.

It is understood that in some aspects, the device can comprise two or more optical cells, each configured to obtain a portion of the aqueous sample and to sequentially measure a spectroscopic signal of each of the portions of the aqueous sample.

In yet other aspects, the device can comprise a temperature controller to control a temperature of the portion of the aqueous sample. Any known in the art temperature controllers can be utilized.

In yet further aspects, the system can further comprise a data analyzer configured to analyze the $pH_{initial}$ value, the $pH_{final}$ value, to determine a specific dissociation constant K of the buffer, and value I. It is understood that the data analyzer can comprise computational capabilities to calculate the desired values.

In still further aspects, the data analyzer can provide an output value comprising one or more of $pH^0$, the specific dissociation constant K of the buffer, and the value I.

Also disclosed is a system for measuring an ionic strength of an aqueous sample comprising: a) a device comprising i) a spectrophotometer; and ii) at least one optical cell configured to obtain the aqueous sample comprising a pH indicator and to measure a $pH_1$ value of the aqueous sample; b) a first dispenser configured to add a first volume of a first buffer solution to obtain a $pH_2$ value of the aqueous sample, wherein the $pH_2$ is lower or higher than $pH_1$, and c) a second dispenser configured to add a second volume of a second buffer solution to obtain a $pH_3$ value of the aqueous sample, wherein the $pH_3$ is substantially equal to $pH_1$.

In still further aspects, the system can further comprise a data analyzer configured to analyze the $pH_1$, $pH_2$, and $pH_3$ values to determine a specific dissociation constant K of the buffer and to calculate a value I.

In yet further aspects, the systems disclosed herein are portable. While yet, in other aspects, the systems disclosed herein are automatic.

The claims are not intended to include, and should not be interpreted to include, means-plus- or step-plus-function limitations, unless such a limitation is explicitly recited in a given claim using the phrase(s) "means for" or "step for," respectively.

In view of the described processes and compositions, hereinbelow are described certain more particularly described aspects of the inventions. These particularly recited aspects should not, however, be interpreted to have any limiting effect on any different claims containing different or more general teachings described herein, or that the "particular" aspects are somehow limited in some way other than the inherent meanings of the language and formulas literally used therein.

Aspects:

Aspect 1: A method comprising n stages for determining an ionic strength I of an aqueous sample, wherein the method comprises: a first of the n stages comprising: a) adding a pH indicator to a portion of the aqueous sample; b) adjusting a pH of the portion of the aqueous sample to obtain a $pH_{initial}$ value; c) adding an amount of a buffer to the portion of the aqueous sample to obtain a $pH_{final}$; d) repeating steps a)-c) for n times, until $pH_{initial}$ is substantially similar to a $pH_{final}$, and is defined as an equilibrium $pH^0$, and wherein a portion of the aqueous sample in step a) of each subsequent stage is a new portion of the aqueous sample; and a $pH_{initial}$ in step b) of each subsequent stage is different from a $pH_{initial}$ of each preceding stage; and e) calculating the I value from a ratio of a total alkalinity of the aqueous sample to a total concentration of the buffer $A_t/[Buffer]_t$, wherein the I value is calculated as a function of a specific dissociation constant K of the buffer; and wherein a temperature of the portion of the aqueous sample at steps b) and c) is substantially identical.

Aspect 2: The method of Aspect 1, wherein the specific dissociation constant K is a function of the value/according to Equation (1):

$$\log_{10} K = A*I^{0.5}/(1+B*I^{0.5}) + D*I + C \tag{1}$$

wherein A is a constant calculated according to an equation (2)

$$A = \frac{1.83 \times 10^6 \, \rho^{1/2}}{(\varepsilon T)^{3/2}} \Delta z^2, \tag{2}$$

wherein $$\Delta z^2 = \Sigma \Delta z_{i(products)}^2 - \Sigma \Delta z_{i(reactants)}^2 \tag{3},$$

B is a constant calculated according to Equation (4):

$$B = \frac{50.29 \times 10^6 \, \rho^{1/2}}{(\varepsilon T)^{1/2}} \alpha; \tag{4}$$

wherein ρ and ε are density and dialectic constants of the water, respectively, at the temperature of the portion, $z_i$ is a charge number; and α is a size of a buffer ion in cm; or wherein B is obtained semi-empirically or wherein B is a linear fitting parameter of Equation (1); D is a fitting parameter of Equation (1), and wherein C is $\log_{10}K^0$, wherein $K^0$ is a specific equilibrium coefficient of the buffer in pure water having I=0 or wherein C is an intercept with axis y found.

Aspect 3: The method of Aspect 1 or 2, wherein the buffer comprises one or more of a bicarbonate buffer, a phosphate buffer, or a borate buffer.

Aspect 4: The method of Aspect 3, wherein the buffer is the bicarbonate buffer $A_t/[\text{Buffer}]_t$ is according to Equation (5):

$$\frac{A_t}{[\text{Buffer}]_t} = \frac{2K_1K_2 + K_1\left[10^{-pH^0}\right]}{K_1K_2 + K_1\left[10^{-pH^0}\right] + \left[10^{-2pH^0}\right]} = 1; \quad (5)$$

wherein $K_1$ and $K_2$ are specific dissociation constants of bicarbonate expressed according to Equation (1).

Aspect 5: The method of Aspect 3, wherein the buffer is the borate buffer $A_t/[\text{Buffer}]_t$ is according to Equation (6):

$$\frac{A_t}{[\text{Buffer}]_t} = \frac{Kborate}{Kborate + \left[10^{-pH^0}\right]} = \frac{1}{2}; \quad (6)$$

wherein $K_{borate}$ is a dissociation constant of borate buffer expressed according to Equation (1).

Aspect 6: The method of Aspect 3, wherein the buffer is the phosphate buffer $A_t/[\text{Buffer}]_t$ is according to Equation (7):

$$\frac{A_t}{[\text{Buffer}]_t} = \frac{2K_1K_2K_3 + K_1K_2\left[10^{-pH^0}\right]}{K_1K_2K_3 + K_1K_2\left[10^{-pH^0}\right] + K_1\left[10^{-pH^0}\right] + \left[10^{-3pH^0}\right]} = X, \quad (7)$$

wherein 0≤X≤2 and a function of a concentration ratio of $H_2PO_4^-$ and $HPO_4^{2-}$.

Aspect 7: The method of any one of Aspects 1-6, wherein each portion in each of the n stages has a substantially similar volume.

Aspect 8: The method of any one of Aspects 1-7, further comprising determining a $pH_{initial'}$ having a lowest value of $pH_{initial}$ values measured at each of n stages, for which adding the amount of buffer in step d) provides for a $pH_{final'}$ value that is lower than the $pH_{initial'}$.

Aspect 9: The method of any one of Aspects 1-8, further comprising determining a $pH_{initial''}$ having a highest value of $pH_{initial}$ values measured at each of n stages, for which adding the amount of buffer in step d) provides for a $pH_{final''}$ value that is higher than a $pH_{initial''}$.

Aspect 10: The method of Aspect 8 or 9, wherein the method further comprises calculating a $pH^0_{i(avg)}$, wherein the $pH^0_{i(avg)}$ is an average of the $pH_{initial'}$ and $pH_{initial''}$.

Aspect 11: The method of Aspect 9 or 10, wherein the method further comprises calculating a $pH^0_{t(avg)}$, wherein the $pH^0_{t(avg)}$ is an average of the $pH_{final'}$ and $pH_{final''}$.

Aspect 12: The method of any one of Aspects 1-11, wherein a temperature of the portion of the aqueous sample at steps c) and d) of each subsequent stage is the same or different.

Aspect 13: The method of any one of Aspects 10-12, wherein at the $pH^0$, the $pH^0_{i(avg)}$ is substantially identical to the $pH^0_{t(avg)}$.

Aspect 14: The method of any one of Aspects 1-13, wherein the buffer is added in an amount effective to introduce substantially no change in the I value.

Aspect 15: The method of any one of Aspects 1-14, wherein the buffer is added as a solid, a solution, or a combination thereof.

Aspect 16: The method of any one of Aspects 1-15, wherein the step c) of adjusting the pH comprises adding an amount of an acid or a base, wherein the amount of the acid or base is effective to introduce substantially no change to the I value of the aqueous sample.

Aspect 17: The method of any one of Aspects 1-16, wherein $pH_{initial}$ and/or $pH_{final}$ are measured spectroscopically.

Aspect 18: The method of any one of Aspects 1-17, wherein the pH indicator comprises a substantially purified sulfonephthalein, bromocresol purple, m-cresol purple, phenylphenol, or thymol blue, bromothymol blue, or chlorophenol red.

Aspect 19: The method of Aspect 17 or 18, wherein the $pH_{initial}$ and/or $pH_{final}$ is measured according to Equation (8):

$$pH' = -_{IN}(\log(K_2^{IN}e_2)) + \log((R-e_1)/(1-Re_4)) \quad (8);$$

wherein pH' is the $pH_{initial}$ and/or $pH_{final}$ of the aqueous sample; $K_2^{IN}$ is an equilibrium constant for a second dissociation step of the pH indicator; R is $A_{\lambda_2}/A_{\lambda_1}$; wherein is $A_{\lambda_1}$ and $A_{\lambda_2}$ are indicator absorbances at $\lambda_1$ and $\lambda_2$ respectively, wherein $\lambda_1$ is a wavelength of absorbance maxima for $HIN^-$ and $\lambda_2$ is a wavelength of absorbance maxima for $IN^{2-}$; $e_1$, $e_2$, $e_3$, and $e_4$ are ratios of molar absorptivity coefficients expressed according to:

$$e_1 = _{\lambda_2}\varepsilon_{HIN^-}/_{\lambda_1}\varepsilon_{HIN^-}$$

$$e_2 = _{\lambda_2}\varepsilon_{IN^{2-}}/_{\lambda_1}\varepsilon_{HIN^-}$$

$$e_3 = _{\lambda_2}\varepsilon_{IN^{2-}}/_{\lambda_1}\varepsilon_{HIN^-}$$

$$e_4 = e_3/e_2 = _{\lambda_2}\varepsilon_{IN^{2-}}/_{\lambda_1}\varepsilon_{IN^{2-}}$$

ε is a molar absorptivity coefficient of a monoprotonated form of the indicator $HIN^-$ or a fully deprotonated form of the indicator $IN^{2-}$ at $\lambda_2$ and $\lambda_1$, respectively; and wherein $_{IN}(\log(K_2^{IN}e_2))$ is determined semi-empirically as a function of the ionic strength and a temperature of the aqueous solution.

Aspect 20: The method of Aspect 19, wherein the pH indicator is thymol blue, the $_{IN}(\log(K_2^{IN}e_2))$ is estimated according to Equation (9):

$$_{IN}(\log(K_2^{IN}e_2)) = \quad (9)$$
$$A + BS_p^{0.5}T + CT^{-0.5}S_p + \frac{D}{T} + ES_p + FS_p^{1.5} + GS_p^2 + HS_p^{2.5}$$

wherein $S_p$ is a salinity of the aqueous sample that is linearly dependent on the ionic strength of the aqueous solution and T is a temperature of the aqueous sample; and wherein A, B, C, D, F, G, and H are parameters that are found in the art or are fitting parameters of Equation (9).

Aspect 21: The method of Aspect 20, wherein the ionic strength for estimation of $S_p$ is measured by a conductivity measurement.

Aspect 22: The method of any one of Aspects 7-21, wherein the volume of the portion of the aqueous sample is from about 1 mL to about 30 mL.

Aspect 23: The method of any one of Aspects 1-22, wherein the temperature of the portion of the aqueous sample is controlled.

Aspect 24: The method of any one of Aspects 1-23, wherein the aqueous sample comprises river water, lake water, or any combination thereof.

Aspect 25: A method for determining an ionic strength I of an aqueous sample, wherein the method comprises: a) measuring a pH of the aqueous sample, wherein the aqueous sample comprises a pH indicator to obtain a $pH_1$ value of the aqueous sample; b) adding a first volume of a first buffer solution to the aqueous sample to arrive at $pH_2$, wherein the $pH_2$ is smaller or higher than $pH_1$; c) adding a second volume of a second buffer solution to the aqueous sample to arrive at $pH_3$, wherein the $pH_3$ is substantially identical to the $pH_1$; and d) determining the I value from a ratio of a total alkalinity of the aqueous sample to a total concentration of the buffer $A_t/[Buffer]_t$, wherein the ratio $A_t/[Buffer]_t$ is provided by a ratio of the first volume and the second volume of the first and the second buffer solutions and by a composition of the first and the second buffer solutions, and wherein the I value is calculated as a function of a specific dissociation constant of the buffer; wherein a temperature of the aqueous sample at steps a) through c) is substantially identical; and wherein the first and the second volumes of the first and second buffer solution do not substantially change the I value of the aqueous sample.

Aspect 26: The method of Aspect 25, wherein the specific dissociation constant K is a function of the value/according to Equation (1):

$$\log_{10} K = A*I^{0.5}/(1+B*I^{0.5})+D*I+C; \quad (1)$$

wherein A is a constant calculated according to an equation (2)

$$A = \frac{1.83 \times 10^6 \, \rho^{1/2}}{(\varepsilon T)^{3/2}} \Delta z^2, \quad (2)$$

wherein $$\Delta z^2 = \Sigma \Delta z_{i(products)}^2 - \Sigma \Delta z_{i(reactants)}^2 \quad (3),$$

B is a constant calculated according to Equation (4):

$$B = \frac{50.29 \times 10^6 \, \rho^{1/2}}{(\varepsilon T)^{1/2}} \alpha; \quad (4)$$

wherein $\rho$ and $\varepsilon$ are density and dialectic constants of the water, respectively, at the temperature of the portion, $z_i$ is a charge number; and $\alpha$ is a size of a buffer ion in cm; or wherein B is obtained semi-empirically or wherein B is a linear fitting parameter of Equation (1); and D is a fitting parameter of Equation (1); and wherein C is $\log_{10} K^0$, wherein $K^0$ is a specific equilibrium coefficient of the buffer in pure water having I=0 or wherein C is an intercept with axis y found.

Aspect 27: The method of Aspect 25 or 26, wherein the first buffer solution and/or the second buffer solution comprises one or more of a bicarbonate buffer, a phosphate buffer, or a borate buffer.

Aspect 28: The method of any one of Aspects 25-27, wherein the first buffer solution comprises $NaH_2PO_4$.

Aspect 29: The method of any one of Aspects 25-28, wherein the second buffer solution comprises $K_2HPO_4$.

Aspect 30: The method of Aspect 27, wherein the buffer is the bicarbonate buffer $A_t/[Buffer]_t$ is according to Equation (4):

$$\frac{A_t}{[Buffer]_t} = \frac{2K_1 K_2 + K_1[10^{-pH^0}]}{K_1 K_2 + K_1[10^{-pH^0}] + [10^{-2pH^0}]} = 1; \quad (5)$$

wherein $K_1$ and $K_2$ are specific dissociation constants of bicarbonate expressed according to Equation (1).

Aspect 31: The method of Aspect 27, wherein the buffer is the borate buffer $A_t/[Buffer]_t$ is according to Equation (6):

$$\frac{A_t}{[Buffer]_t} = \frac{Kborate}{Kborate + [10^{-pH^0}]} = \frac{1}{2}; \quad (6)$$

wherein $K_{borate}$ is a dissociation constant of borate buffer expressed according to Equation (1).

Aspect 32: The method of Aspect 27, wherein the buffer is the phosphate buffer $A_t/[Buffer]_t$ is according to Equation (7):

$$\frac{A_t}{[Buffer]_t} = \frac{2K_1 K_2 K_3 + K_1 K_2[10^{-pH^0}]}{K_1 K_2 K_3 + K_1 K_2[10^{-pH^0}] + K_1[10^{-pH^0}] + [10^{-3pH^0}]} = X, \quad (7)$$

wherein $0 \leq X \leq 2$ and depends on a concentration ratio of $H_2PO_4^-$ and $HPO_4^{2-}$.

Aspect 33: The method of any one of Aspects 25-32, wherein $pH_1$, $pH_2$, and $pH_3$ are measured spectroscopically.

Aspect 34: The method of any one of Aspects 25-33, wherein the pH indicator comprises a substantially purified sulfonephthalein, bromocresol purple, m-cresol purple, phenylphenol, or thymol blue, bromothymol blue, or chlorophenol red.

Aspect 35: The method of any one of Aspects 33-34, wherein the $pH_1$, $pH_2$, and $pH_3$ are measured according to Equation (8):

$$pH' = -_{IN}(\log(K_2^{IN}e_2)) + \log((R-e_1)/(1-Re_4)) \quad (8);$$

wherein pH' is the $pH_1$, $pH_2$, and $pH_3$ of the aqueous sample; $K_2^{IN}$ is an equilibrium constant for a second dissociation step of the pH indicator; R is $A_{\lambda_2}/A_{\lambda_1}$; wherein is $A_{\lambda_1}$ and $A_{\lambda_2}$ are indicator absorbances at $\lambda_1$ and $\lambda_2$ respectively, wherein $\lambda_1$ is a wavelength of absorbance maxima for $HIN^-$ and $\lambda_2$ is a wavelength of absorbance maxima for $IN^{2-}$; $e_1$, $e_2$, $e_3$, and $e_4$ are ratios of molar absorptivity coefficients expressed according to:

$$e_1 = _{\lambda_2}\varepsilon_{HIN^-}/_{\lambda_1}\varepsilon_{HIN^-}$$

$$e_2 = _{\lambda_2}\varepsilon_{IN^{2-}}/_{\lambda_1}\varepsilon_{HIN^-}$$

$$e_3 = _{\lambda_2}\varepsilon_{IN^{2-}}/_{\lambda_1}\varepsilon_{HIN^-}$$

$$e_4 = e_3/e_2 = _{\lambda_2}\varepsilon_{IN^{2-}}/_{\lambda_1}\varepsilon_{IN^{2-}}$$

$\varepsilon$ is a molar absorptivity coefficient of a monoprotonated form of the indicator $HIN^-$ or a fully deprotonated form of the indicator $IN^{2-}$ at $\lambda_2$ and $\lambda_1$, respectively; and wherein $_{IN}(\log(K_2^{IN}e_2))$ is determined semi-empirically as a function of the ionic strength and a temperature of the aqueous solution.

Aspect 36: The method of Aspect 35, wherein the pH indicator is thymol blue, the $_{IN}(\log(K_2^{IN}e_2))$ is estimated according to Equation (9):

$$_{IN}(\log(K_2^{IN}e_2)) = \qquad (9)$$
$$A + BS_p^{0.5}T + CT^{-0.5}S_p + \frac{D}{T} + ES_p + FS_p^{1.5} + GS_p^2 + HS_p^{2.5}$$

wherein $S_p$ is a salinity of the aqueous sample that is linearly dependent on the ionic strength of the aqueous solution and T is a temperature of the aqueous sample; and wherein A, B, C, D, F, G, and H are parameters that are found in the art or are fitting parameters of Equation (9).

Aspect 37: The method of Aspect 36, wherein the ionic strength for estimation of $S_p$ is measured by a conductivity measurement.

Aspect 38: The method of any one of Aspects 25-37, wherein the aqueous sample comprises river water, lake water, or any combination thereof.

Aspect 39: A system for measuring an ionic strength of an aqueous sample comprising: a) a device comprising i) a spectrophotometer; and ii) at least one optical cell configured to obtain a portion of the aqueous sample, wherein the portion of the aqueous sample has a predetermined volume; b) a first dispenser configured to add an amount of an acid or a base to the portion of the aqueous sample to obtain a $pH_{initial}$ value; c) a second dispenser configured to add an amount of a buffer to the portion of the aqueous sample to obtain a $pH_{final}$.

Aspect 40: The system of Aspect 39, wherein the device comprises two or more optical cells, each configured to obtain a portion of the aqueous sample and to sequentially measure a spectroscopic signal of each of the portions of the aqueous sample.

Aspect 41: The system of Aspect 39 or 40, wherein the device comprises a temperature controller to control a temperature of the portion of the aqueous sample.

Aspect 42: The system of claim any one of Aspects 39-41 wherein the system further comprises a data analyzer configured to analyze the $pH_{initial}$ value, the $pH_{final}$ value, to determine a specific dissociation constant K of the buffer, and a value I.

Aspect 43: The system of Aspect 42, wherein the data analyzer provides an output value comprising one or more of $pH^0$, the specific dissociation constant K of the buffer, and the value I.

Aspect 44: A system for measuring an ionic strength of an aqueous sample comprising: a) a device comprising i) a spectrophotometer; and ii) at least one optical cell configured to obtain the aqueous sample comprising a pH indicator and to measure a $pH_1$ value of the aqueous sample; b) a first dispenser configured to add a first volume of a first buffer solution to obtain a $pH_2$ value of the aqueous sample, wherein the $pH_2$ is lower or higher than $pH_1$, and c) a second dispenser configured to add a second volume of a second buffer solution to obtain a $pH_3$ value of the aqueous sample, wherein the $pH_3$ is substantially equal to $pH_1$.

Aspect 45: The system of Aspect 44, wherein the device comprises two or more optical cells, each configured to obtain the aqueous sample and to sequentially measure a spectroscopic signal of each of the aqueous samples.

Aspect 46: The system of Aspect 44 or 45, wherein the device comprises a temperature controller to control a temperature of the aqueous sample.

Aspect 47: The system of any one of Aspects 44-46 wherein the system further comprises a data analyzer configured to analyze the $pH_1$, $pH_2$, and $pH_3$ values to determine a specific dissociation constant K of the buffer and to calculate a value I.

Aspect 48: The system of Aspect 47, wherein the data analyzer provides an output value comprising the value I.

Aspect 49: The system of any one of Aspects 39-48, wherein the system is portable.

Aspect 50: The system of any one of Aspects 39-49, wherein the system is automatic.

What is claimed is:

1. A method comprising n stages for determining an ionic strength I of an aqueous sample, wherein the method comprises:

a first of the n stages comprising:
  a) adding a pH indicator to a portion of the aqueous sample;
  b) adjusting a pH of the portion of the aqueous sample to obtain a $pH_{initial}$ value;
  c) adding an amount of a buffer to the portion of the aqueous sample to obtain a $pH_{final}$;
  d) repeating steps a)-c) for n times, until $pH_{initial}$ is substantially similar to a $pH_{final}$, and is defined as an equilibrium $pH^0$, and wherein
    a portion of the aqueous sample in step a) of each subsequent stage is a new portion of the aqueous sample; and
    a $pH_{initial}$ in step b) of each subsequent stage is different from a $pH_{initial}$ of each preceding stage; and
  e) calculating the I value from a ratio of a total alkalinity of the aqueous sample to a total concentration of the buffer $A_t$/[Buffer]$_t$, wherein the I value is calculated as a function of a specific dissociation constant K of the buffer; and
wherein a temperature of the portion of the aqueous sample at steps b) and c) is substantially identical.

2. The method of claim 1, wherein the specific dissociation constant K is a function of the value I according to Equation (1):

$$\log_{10} K = A*I^{0.5}/(1+B*I^{0.5})+D*I+C \qquad (1) \text{ wherein}$$

A is a constant calculated according to an equation (2)

$$A = \frac{1.83 \times 10^6 \, \rho^{1/2}}{(\varepsilon T)^{3/2}} \Delta z^2, \qquad (2)$$

wherein $$\Delta z^2 = \Sigma \Delta z_{i(products)}^2 - \Sigma \Delta z_{i(reactants)}^2 \qquad (3)$$

B is a constant calculated according to Equation (4):

$$B = \frac{50.29 \times 10^6 \, \rho^{1/2}}{(\varepsilon T)^{1/2}} \alpha; \qquad (4)$$

wherein ρ and ε are density and dialectic constants of the water, respectively, at the temperature of the portion, $z_i$ is a charge number; and a is a size of a buffer ion in cm; or wherein B is obtained semi-empirically or wherein B is a linear fitting parameter of Equation (1); and D is a fitting parameter of Equation (1); and wherein C is $\log_{10} K^0$, wherein $K^0$ is a specific equilibrium coefficient of the buffer in pure water having I=0 or wherein C is an intercept with axis y found.

3. The method of claim 2, wherein the buffer is a bicarbonate buffer and wherein the $A_t/[\text{Buffer}]_t$ is according to Equation (5):

$$\frac{A_t}{[\text{Buffer}]_t} = \frac{2K_1 K_2 + K_1[10^{-pH^0}]}{K_1 K_2 + K_1[10^{-pH^0}] + [10^{-2pH^0}]} = 1; \quad (5)$$

wherein $K_1$ and $K_2$ are specific dissociation constants of bicarbonate expressed according to Equation (1).

4. The method of claim 2, wherein the buffer is a borate buffer and wherein the $A_t/[\text{Buffer}]_t$ is according to Equation (6):

$$\frac{A_t}{[\text{Buffer}]_t} = \frac{K_{borate}}{K_{borate} + [10^{-pH^0}]} = \frac{1}{2}; \quad (6)$$

wherein $K_{borate}$ is a dissociation constant of borate buffer expressed according to Equation (1).

5. The method of claim 2, wherein the buffer is a phosphate buffer and wherein the $A_t/[\text{Buffer}]_t$ is according to Equation (7):

$$\frac{A_t}{[\text{Buffer}]_t} = \frac{2K_1 K_2 K_3 + K_1 K_2[10^{-pH^0}]}{K_1 K_2 K_3 + K_1 K_2[10^{-pH^0}] + K_1[10^{-pH^0}] + [10^{-3pH^0}]} = X, \quad (7)$$

wherein $0 \leq X \leq 2$ and a function of a concentration ratio of $H_2PO_4^-$ and $HPO_4^{2-}$.

6. The method of claim 1, further comprising determining a $pH_{initial'}$ having a lowest value of $pH_{initial}$ values measured at each of n stages, for which adding the amount of buffer in step d) provides for a $pH_{final'}$ value that is lower than the $pH_{initial'}$.

7. The method of claim 1, further comprising determining a $pH_{initial''}$ having a highest value of $pH_{initial}$ values measured at each of n stages, for which adding the amount of buffer in step d) provides for a $pH_{final''}$ value that is higher than a $pH_{initial'''}$.

8. The method of claim 7, wherein the method further comprises calculating a $pH^0_{i(avg)}$, wherein the $pH^0_{i(avg)}$ is an average of the $pH_{initial'}$ and $pH_{initiaL''}$, and wherein the method further comprises calculating a $pH^0_{f(avg)}$, wherein the $pH^0_{f(avg)}$ is an average of the $pH_{final'}$ and $pH_{final''}$.

9. The method of claim 8, wherein at the $pH^0$, the $pH^0_{i(avg)}$ is substantially identical to the $pH^0_{f(avg)}$.

10. The method of claim 1, wherein the buffer is added in an amount effective to introduce substantially no change in the I value.

11. The method of claim 1 wherein step c) of adjusting the pH comprises adding an amount of an acid or a base, wherein the amount of the acid or base is effective to introduce substantially no change to the I value of the aqueous sample.

12. The method of claim 1, wherein $pH_{initial}$ and/or $pH_{final}$ are measured spectroscopically.

13. The method of claim 12, wherein the $pH_{initial}$ and/or pHfinai is measured according to Equation (8):

$$pH' = -_{IN}(\log(K_2^{IN} e_2)) + \log((R - e_1)/(1 - Re_4)) \quad (8);$$

wherein pH' is the $pH_{initial}$ and/or $pH_{final}$ of the aqueous sample; $K_2^{IN}$ is an equilibrium constant for a second dissociation step of the pH indicator;

R is $A_{\lambda_2}/A_{\lambda_1}$; wherein is $A_{\lambda_1}$ and $A_{\lambda_2}$ are indicator absorbances at $\lambda_1$ and $\lambda_2$ respectively, wherein $\lambda_1$ is a wavelength of absorbance maxima for HIN$^-$ and $\lambda_2$ is a wavelength of absorbance maxima for IN$^{2-}$;

$e_1$, $e_2$, $e_3$, and $e_4$ are ratios of molar absorptivity coefficients expressed according to:

$e_1 = _{\lambda_2}\varepsilon_{HIN^-}/_{\lambda_1}\varepsilon_{HIN^-}$ $e_2 = _{\lambda_2}\varepsilon_{IN^{2-}}/_{\lambda_1}\varepsilon_{HIN^-}$ $e_3 = _{\lambda_2}\varepsilon_{IN^{2-}}/_{\lambda_1}\varepsilon_{HIN^-}$ $e_4 = e_3/e_2 = _{\lambda_2}\varepsilon_{IN^{2-}}/_{\lambda_1}\varepsilon_{IN^{2-}}$ ε is a molar absorptivity coefficient of a monoprotonated form of the indicator HIN$^-$ or a fully deprotonated form of the indicator IN$^{2-}$ at $\lambda_2$ and $\lambda_1$, respectively;

and wherein $_{IN}(\log(K_2^{IN} e_2))$ is determined semi-empirically as a function of the ionic strength and a temperature of the aqueous solution.

14. The method of claim 13, wherein a pH indicator is thymol blue, the $_{IN}(\log(K_2^{IN} e_2))$ is estimated according to Equation (9):

$$_{IN}(\log(K_2^{IN} e_2)) = \quad (9)$$
$$A + BS_p^{0.5} T + CT^{-0.5} S_p + \frac{D}{T} + ES_p + FS_p^{1.5} + GS_p^2 + HS_p^{2.5}$$

wherein $S_p$ is a salinity of the aqueous sample that is linearly dependent on the ionic strength of the aqueous solution and T is a temperature of the aqueous sample; and wherein A, B, C, D, F, G, and H are parameters that are found in the art or are fitting parameters of Equation (9).

15. The method of claim 14, wherein the ionic strength for estimation of $S_p$ is measured by a conductivity measurement.

16. The method of claim 1, wherein the aqueous sample comprises river water, lake water, or any combination thereof.

17. A method for determining an ionic strength I of an aqueous sample, wherein the method comprises:
a) measuring a pH of the aqueous sample, wherein the aqueous sample comprises a pH indicator to obtain a $pH_1$ value of the aqueous sample;
b) adding a first volume of a first buffer solution to the aqueous sample to arrive at $pH_2$, wherein the $pH_2$ is smaller or higher than $pH_1$;
c) adding a second volume of a second buffer solution to the aqueous sample to arrive at $pH_3$, wherein the $pH_3$ is substantially identical to the $pH_1$; and
d) determining the I value from a ratio of a total alkalinity of the aqueous sample to a total concentration of the buffer $A_t/[\text{Buffer}]_t$, wherein the ratio $A_t/[\text{Buffer}]_t$ is provided by a ratio of the first volume and the second volume of the first and the second buffer solutions and by a composition of the first and the second buffer solutions, and wherein the I value is calculated as a function of a specific dissociation constant of the buffer;

wherein a temperature of the aqueous sample at steps a) through c) is substantially identical; and wherein the first and the second volumes of the first and second buffer solution do not substantially change the I value of the aqueous sample; and wherein the specific dissociation constant K is a function of the value I according to Equation (1):

$$\log_{10} K = A*I^{0.5}/(1+B*I^{0.5}) + D*I + C \quad (1)$$

wherein A is a constant calculated according to an equation (2)

$$A = \frac{1.83 \times 10^6 \, \rho^{1/2}}{(\varepsilon T)^{3/2}} \Delta z^2, \quad (2)$$

wherein $$\Delta z^2 = \Sigma \Delta z_{i(products)}^2 - \Sigma \Delta z_{i(reactants)}^2 \quad (3)$$

B is a constant calculated according to Equation (4):

$$B = \frac{50.29 \times 10^6 \, \rho^{1/2}}{(\varepsilon T)^{1/2}} \alpha; \quad (4)$$

wherein $\rho$ and $\varepsilon$ are density and dialectic constants of the water, respectively, at the temperature of the portion, $z_i$ is a charge number; and a is a size of a buffer ion in cm; or wherein B is obtained semi-empirically or wherein B is a linear fitting parameter of Equation (1);

D is a fitting parameter of Equation (1); and wherein

C is $\log_{10} K^0$, wherein $K^0$ is a specific equilibrium coefficient of the buffer in pure water having I=0 or wherein C is an intercept with axis y found.

18. The method of claim 17, wherein the $pH_1$, $pH_2$, and $pH_3$ are measured according to Equation (8):

$$pH' = -_{IN}(\log(K_2^{IN}e_2)) + \log((R-e_1)/(1-Re_4)) \quad (8);$$

wherein pH' is the $pH_1$, $pH_2$, and $pH_3$ of the aqueous sample; $K_2^{IN}$ is an equilibrium constant for a second dissociation step of a pH indicator;

R is $A_{\lambda_2}/A_{\lambda_1}$; wherein is $A_{\lambda_1}$ and $A_{\lambda_2}$ are indicator absorbances at $\lambda_1$ and $\lambda_2$ respectively, wherein $\lambda_1$ is a wavelength of absorbance maxima for $HIN^-$ and $\lambda_2$ is a wavelength of absorbance maxima for $IN^{2-}$;

$e_1$, $e_2$, $e_3$, and $e_4$ are ratios of molar absorptivity coefficients expressed according to:

$$e_1 = _{\lambda_2}\varepsilon_{HIN^-}/_{\lambda_1}\varepsilon_{HIN^-}$$

$$e_2 = _{\lambda_2}\varepsilon_{IN^{2-}}/_{\lambda_1}\varepsilon_{HIN^-}$$

$$e_3 = _{\lambda_2}\varepsilon_{IN^{2-}}/_{\lambda_1}\varepsilon_{HIN^-}$$

$$e_4 = e_3/e_2 = _{\lambda_2}\varepsilon_{IN^{2-}}/_{\lambda_1}\varepsilon_{IN^{2-}}$$

$\varepsilon$ is a molar absorptivity coefficient of a monoprotonated form of the indicator $HIN^-$ or a fully deprotonated form of the indicator $IN^{2-}$ at $\lambda_2$ and $\lambda_1$, respectively;

and wherein $_{IN}(\log(K_2^{IN}e_2))$ is determined semi-empirically as a function of the ionic strength and a temperature of the aqueous solution.

* * * * *